United States Patent [19]
Billiet

[11] Patent Number: 6,004,275
[45] Date of Patent: Dec. 21, 1999

[54] SYSTEM FOR THE MEASUREMENT OF CONTINUOUS CARDIAC OUTPUT

[76] Inventor: Erik Billiet, Eedstraat 11, B-9810 Eke, Belgium

[21] Appl. No.: 08/930,932

[22] PCT Filed: Apr. 15, 1996

[86] PCT No.: PCT/BE96/00043

§ 371 Date: Oct. 10, 1997

§ 102(e) Date: Oct. 10, 1997

[87] PCT Pub. No.: WO96/32056

PCT Pub. Date: Oct. 17, 1996

[30] Foreign Application Priority Data

Apr. 14, 1995 [BE] Belgium .................................. 9500349

[51] Int. Cl.⁶ ............................................. A61B 5/00
[52] U.S. Cl. ............................................. 600/505; 600/526
[58] Field of Search ................................. 600/486, 488, 600/505, 526, 561

[56] References Cited

U.S. PATENT DOCUMENTS

| | | |
|---|---|---|
| Re. 33,283 | 7/1990 | Hollingsead et al. . |
| Re. 33,360 | 10/1990 | Reynolds et al. . |
| 4,730,623 | 3/1988 | Lee .......................................... 600/505 |
| 4,941,475 | 7/1990 | Williams et al. ......................... 600/505 |
| 5,009,234 | 4/1991 | Alt ........................................... 600/505 |
| 5,383,468 | 1/1995 | Nakayama et al. ...................... 600/505 |
| 5,611,338 | 3/1997 | Gallup et al. ............................ 600/505 |
| 5,865,801 | 2/1999 | Houser ..................................... 600/488 |

FOREIGN PATENT DOCUMENTS

| | | |
|---|---|---|
| 0297675 | 1/1989 | European Pat. Off. . |
| 0363117 | 4/1990 | European Pat. Off. . |

OTHER PUBLICATIONS

Murgo et al., Physiologic Signal Acquisition and Processing for Human Hemodynamic Research in a Clinical Cardiac–Catheterization Laboratory., Proceedings Of The IEEE, vol. 65, No. 5 (May 1977): pp. 696–702.

Grossman, and Baim, Diagnostic Cardiac Catheterization and Angiography, Harrison's Principles of Internal Medicine 13th ed., (McGraw–Hill 1993): pp. 979–985.

Primary Examiner—Robert L. Nasser
Attorney, Agent, or Firm—Cooper & Dunham LLP

[57] ABSTRACT

An apparatus is in development which measures the blood outflow through the heart valves by means of the bolus thermodilution method and which from then on measures the continuous cardiac output, considering the formula of Gorlin and the measurement of the blood pressure in the compartments of the heart.

12 Claims, 4 Drawing Sheets

SYSTEM FOR THE MEASUREMENT OF CONTINUOUS CARDIAC OUTPUT

The invention relates to an apparatus for the continuous measurement of the cardiac output without indicator using a flow directed thermodilution catheter comprising of:
- a distal pressure lumen located at the distal end of catheter and which is adapted for measuring the pressure in the arteria pulmonalis;
- a proximal pressure lumen located at about 30 cm of said distal end of the catheter and which is adapted for measuring the pressure of the right atrium;
- a proximal pressure lumen located at about 10 cm of said distal end of the catheter and which is adapted for measuring the pressure of the right ventricle;
- a thermistor located in the arteria pulmonalis at about 4 cm of said distal end of catheter;
- a balloon in order to measure the wedge pressure by means of lumen, when the balloon is inflated, through lumen;
- pressure tubing lines connected to lumen and of catheter and which are filled with sterilized fluid;
- pressure transducers which are connected to said pressure tubing lines and which are adapted for measuring the pressure based on the Wheatstone bridge principles in order to continuously measure:
  - the pressure in the right atrium;
  - the pressure in the right ventricle;
  - the pressure in the pulmonary artery and the wedge pressure at discrete time intervals, at the moment the balloon is inflated.

The most important application of this invention will be found in Intensive Care, Operation Room, Heart catheterisation laboratories, Emergency Room and hospital units where the cardiac activity of very ill patients must be continuously followed with the help of hemodynamic monitoring.

Flow-directed catheters of the so called Swan-Ganz type are described in document EP-A-0363117. The flow directed catheter has a balloon which is inflated during the insertion of the catheter into the patient in order to lead the catheter through the heart valves into the arteria pulmonis. The balloon also makes it possible to measure the wedge pressure when inflated at the PA position, without displacement of the catheter. This type of catheter has several lumina, in order to measure the intracardiac pressures and intermittently the cardiac output by means of bolus thermodilution and in order to take bloodsamples.

This total set-up makes it possible to diagnose the patient's health condition. However measuring Cardiac Output continuously is not possible, as this measurement is restricted because of the limitation of the total amount of blouses (normal single bolus volume is 10 cc) which can be injected into the patient to measure the bolus thermodilution cardiac output.

The thermodilution cardiac output measurement is an accepted, well known technique to measure the cardiac output of a patient. To execute this technique a so called Swan-Ganz catheter is introduced into the patient in a large vein, e.g. vena jugularis, vena subclavia or vena femoralis. The catheter is then placed with its tip (distal end) in the pulmonary artery. Through an opening at about 30 cm of the distal end, a bolus of 10 cc physiologic fluid solution of NaCl 0.9% with a known temperature is injected into the right atrium. A temperature senor in the pulmonary artery (approx. 26 cm distal of the injection site and about 4 cm from the distal end of the catheter) measure the temperature change and the temperature difference compared to the injected bolus temperature.

With a catheter placed in a vein or an artery the blood pressure can be measured directly. The catheter is connected to a so called pressure set, which is also filled up with fluid and which is connected to a pressure transducer. The pressure transducer is connected to an electronics device, also called hemodynamic monitor, which computers the pressure values and displays them on a screen, together with the dynamic pressure wave signal.

Also known is the measurement of contractility of the heart whereby a series of catheters of the so called Swan-Ganz type using pressure sensitive tip transducers are lead into several cavities of the heart, in order to measure various intracardial pressures. This measurement is executed in the left heart more precisely in the left atrium, the left ventricle and aorta, which gives information about overall and regional ventricle functions. Registration of the blood pressures is included in this method.

In a later stage volume-sensitive transducers have been used during the catheterisation to obtain the total pressure-volume curve. Doing so, the pressure-volume curve is registered over one heart cycle, with the end diastolic pressure value defined as one point within the curve.

To obtain the total curve, the measurement is repeated with several pre- and afterload conditions, e.g. by vena cava inferior clamping.

The problem however with these method is the complexity of the left heart invasive pressure measurement, which makes it useless for daily practice.

Also known is the computation of the heart preload by means of the end-diastolic pressure measurement in the left heart.

Execution of this method is obtained again by means of a Swan Ganz catheter, which is filled with fluid and which is connected to a pressure manometer resulting in the measurement of the pressure at the input of the catheter.

The method to measurement the blood flow resistance through the heart valves is described by Kurt J. Isselbacher et al: "Harrisons' principals of internal medicine", page 985, 13th edition, 1993, Mc Graw-Hill Inc.

Using the discontinual but simultaneous measurement of blood pressure and cardiac output, one can derive the value of resistance against flow in the heart as well as in the arterial and venous blood-vessels. The area of the surface can be calculated with the formula of Gorlin:

$$A = \frac{Q}{K\sqrt{\Delta P}}$$

with
- A=the surface of the valve's orifice ($cm^2$)
- Q=the flow through the valve (ml/min)
- ΔP=the mean pressure difference during the throughflow (mmHg)
- K=a constant value of 44.3 for the aortic valve and a value of 37.3 for the mitralis valve.

Applied to the right heart, this formula leads to the following interpretation of Gorlin:

$$Q_H = A_{TR} K_1 \sqrt{\Delta P_{TR}}$$

with
- $Q_H$=the cardiac output $A_{TR}$=the real throughflow surface of the tricuspid valve, which is patient dependent $K_1$=a constant value, which is patient dependent $\Delta P_{TR}$=the means pressure difference over the tricuspid valve at the time of outflow from the right atrium towards the right ventricle through the tricuspid orifice.

Set $A_{TR}K_1$ equal to a factor $Q_{I,TR}$, which we call the cardiac output-coefficient of the individual I, then the formula of Gorlin is replaced by:

$$Q_H = Q_{I,TR} \sqrt{\Delta P_{TR}} \qquad [6]$$

with $Q_H$, $Q_{I,TR}$ en $\Delta P_{TR}$ as described before.

The invention assumes that once the resistance against flow has been defined, it will stay stable over a longer time, under certain conditions, and therefore can be used as a calibration parameter for the continuous cardiac output measurement based on the measurement of pressure difference between the compartments of the heart.

To measure the compartment pressures and to calculate the continuous cardiac output, this invention suggests an apparatus as defined in claim 1 and which measures the hemodynamic parameters and computes continuously the cardiac output, as follows:

a first value consisting in the pressure difference over the tricuspid valve as the pressure difference between right atrium and right ventricle during the out-flow or diastolic period;

a second value consisting in the pressure difference over the pulmonary artery valve as the pressure difference between right ventricle and pulmonary artery during the out-flow or systolic period;

and a third value consisting in the cardiac output in a non-continuous manner by means of thermodilution cardiac output obtained from said thermistor;

and with said three values the calibration value, defining a cardiac output coefficient of an individual.

In other words, once $Q_{I,TR}$ has been calculated, it suffices to measure in a continuous way the value of $\Delta P_{TR}$ to derive the continuous cardiac output $Q_H$.

These features and other features of the invention will further on be described, with reference to the enclosed drawings, which are added as an example.

In these drawings.

In these figures, the same reference numerals are used for corresponding elements.

Figure 1:
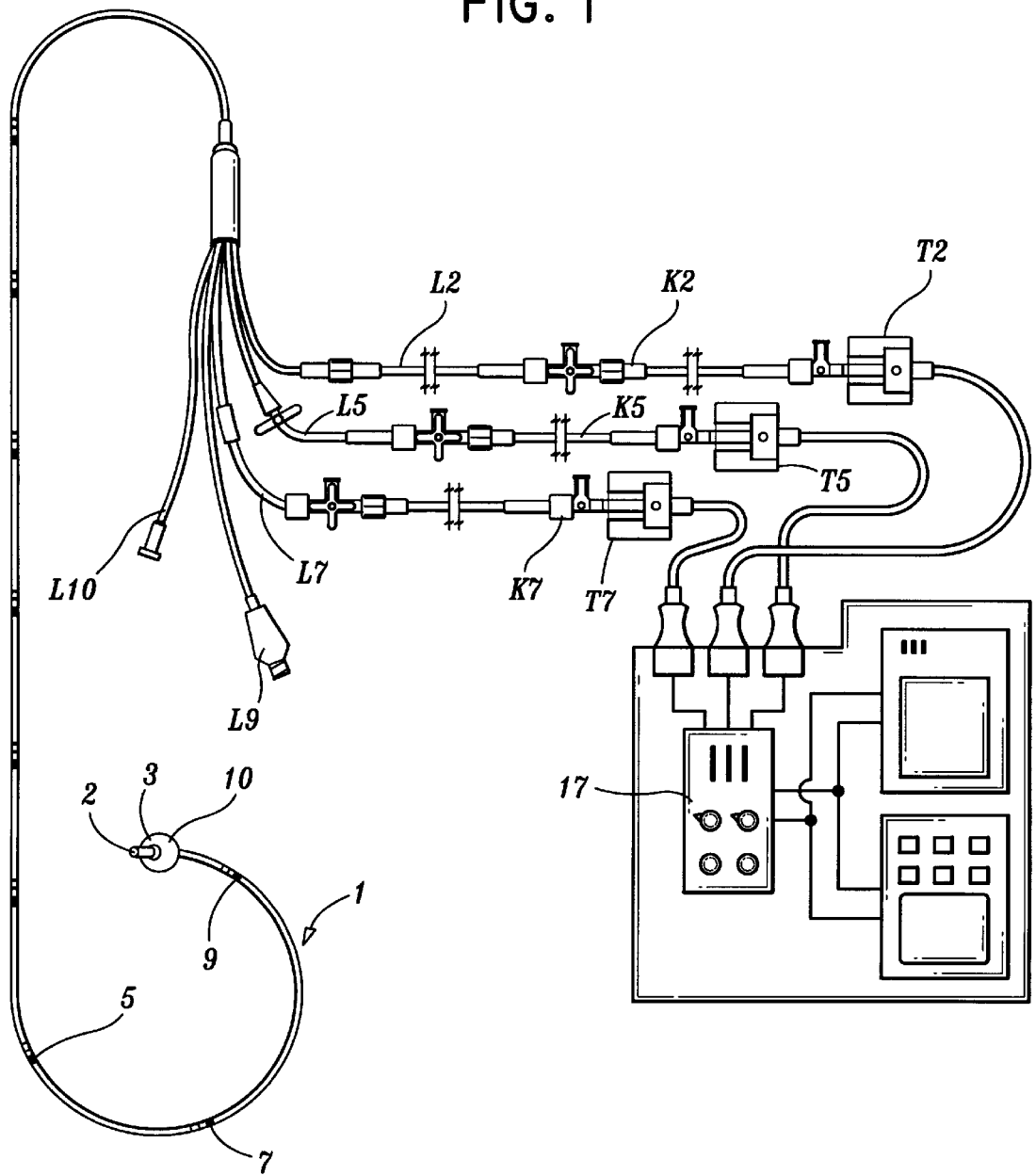
FIG. 1 shows a practical lay-out of the apparatus for the continuous measurement of the cardiac output, by means of the invention.
Figure 2:
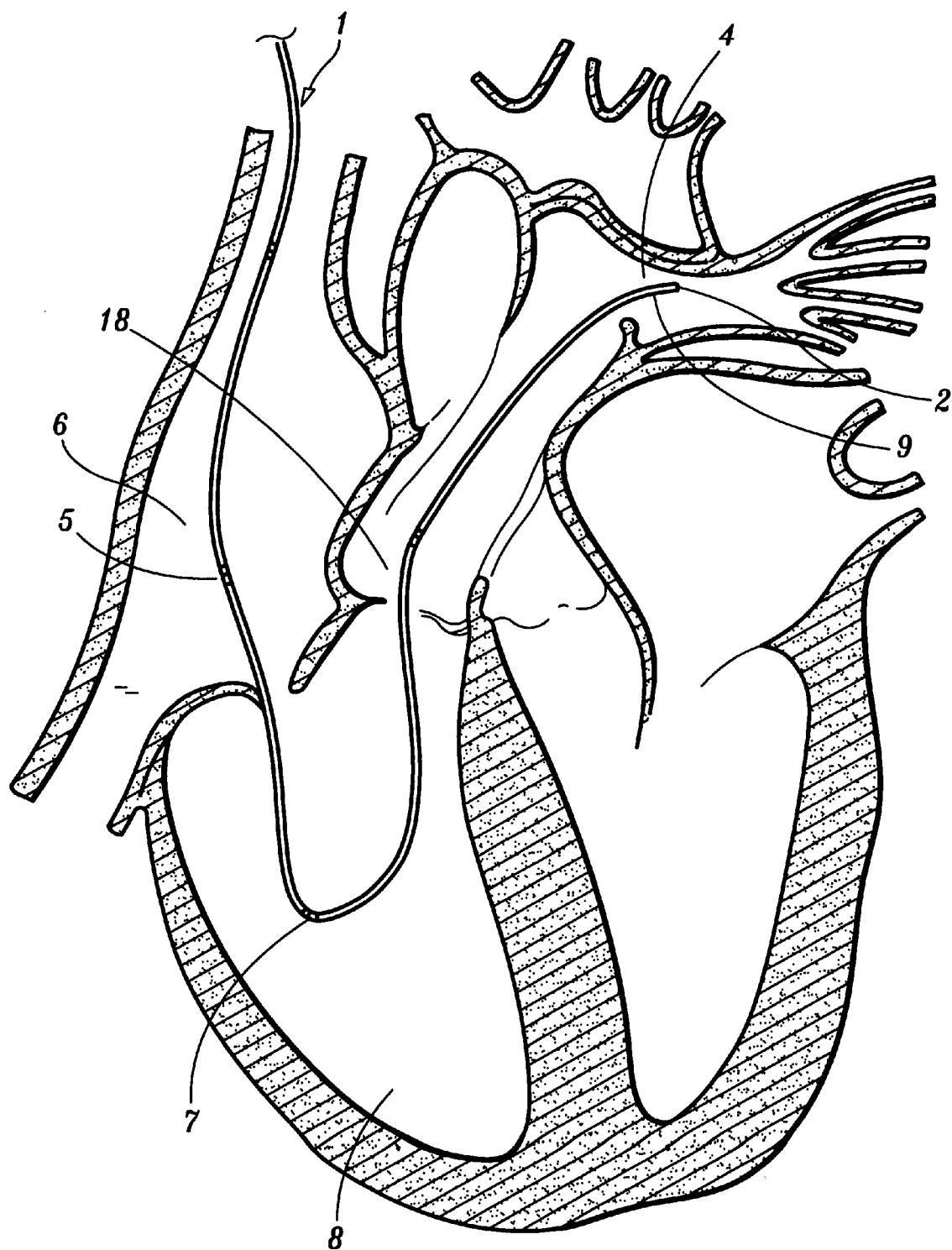
FIG. 2 shows a heart section with indication of the locations of the catheter and the different lumina.
Figure 3A:
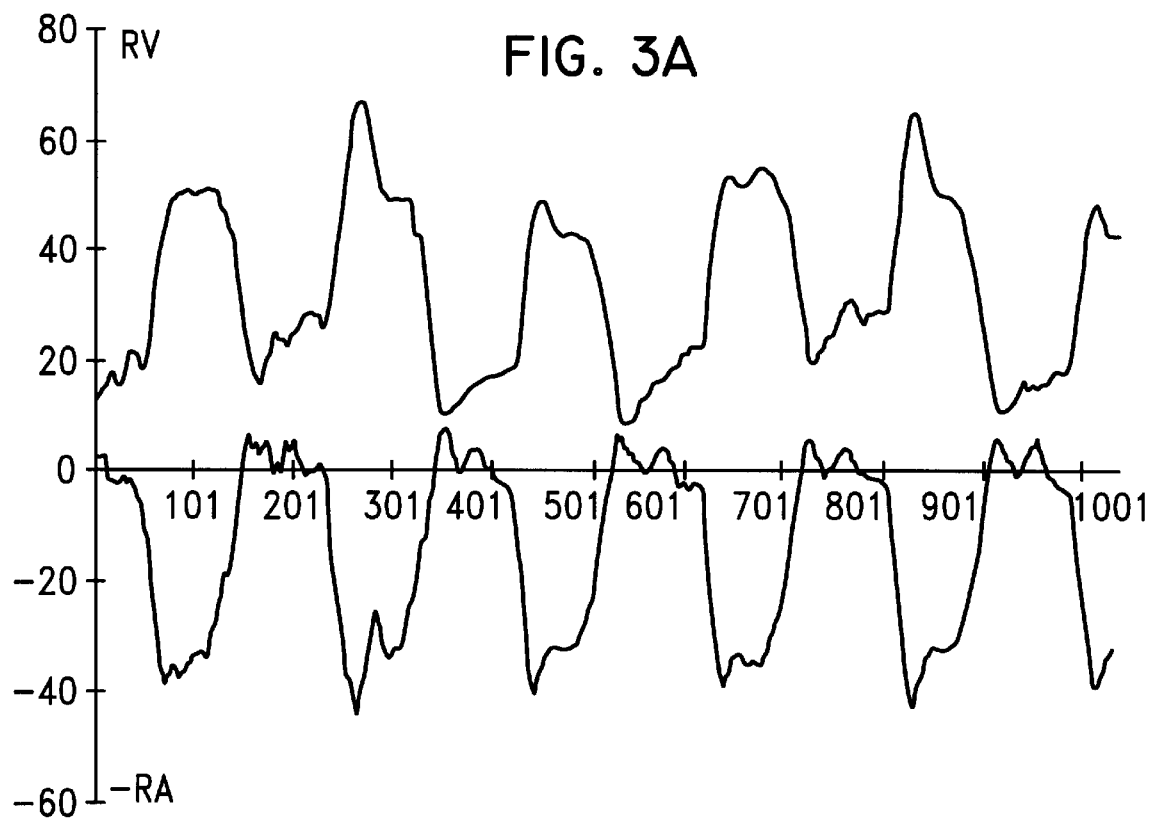
FIG. 3 is a printout of some pressure signals.
Figure 3B:
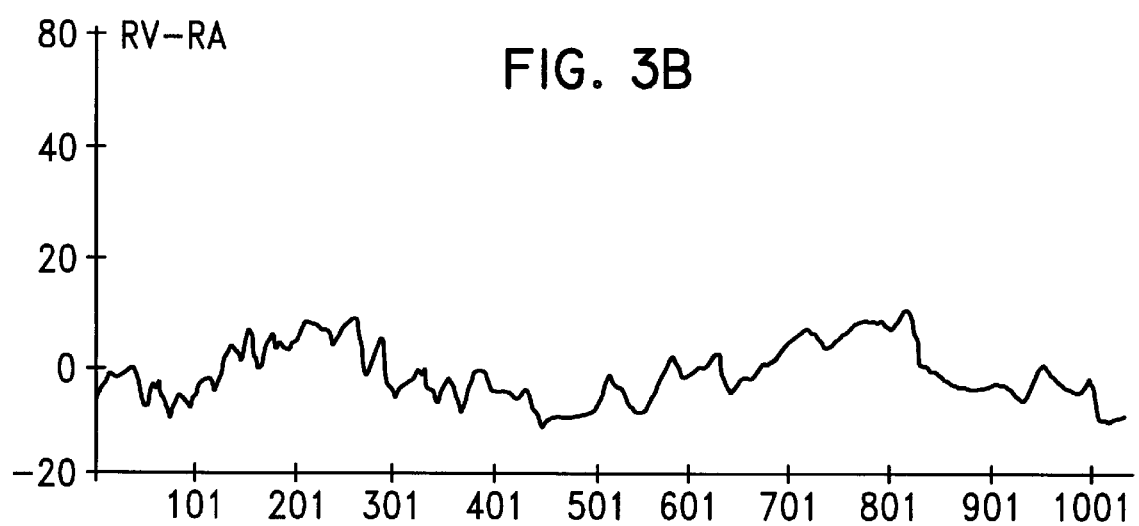
Figure 4:
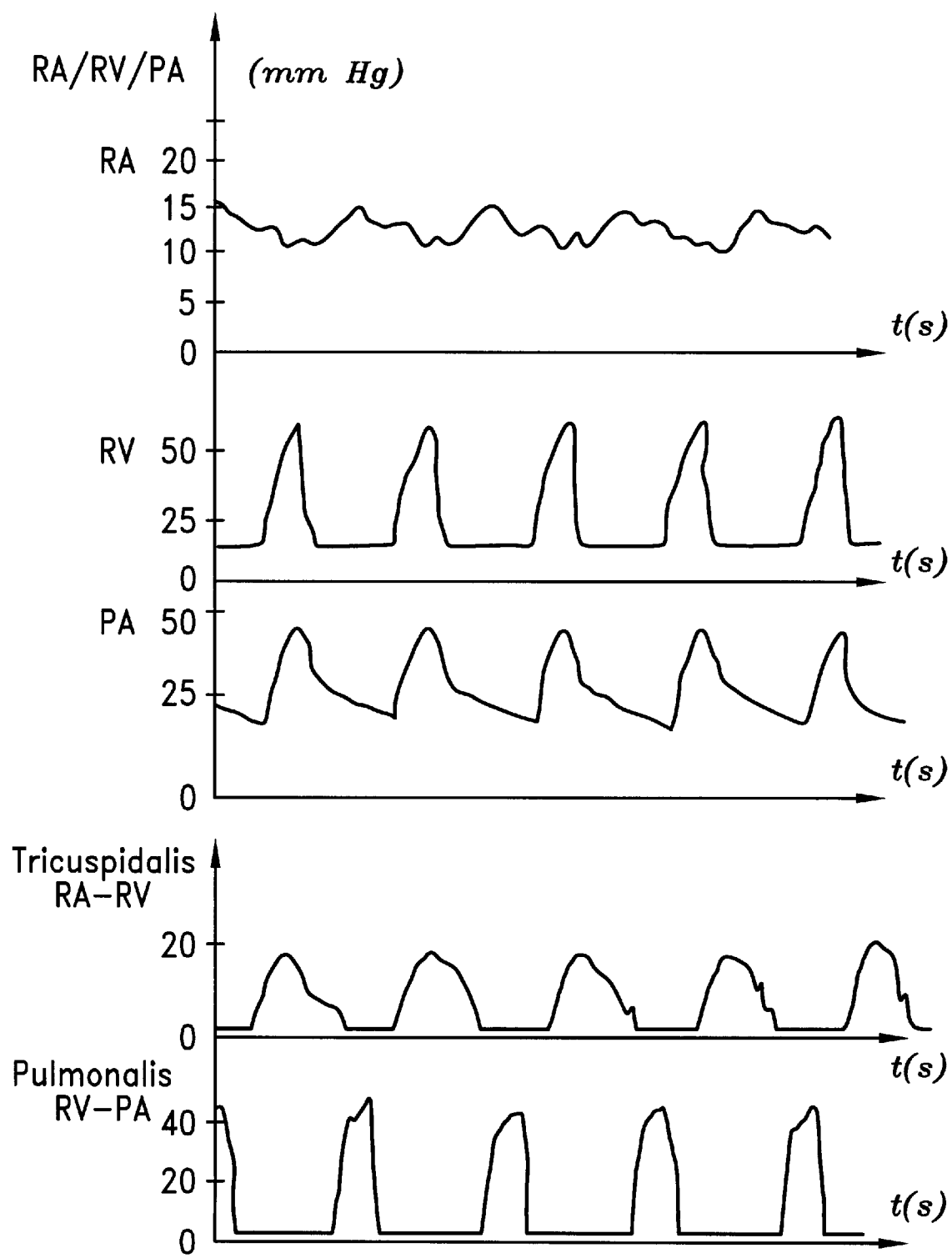
FIG. 4 is a display lay-out of the apparatus.

As shown in FIGS. 1 and 2, an apparatus for the continuous measurement of cardiac output with the help of the flow-directed catheter 1 comprises:

a distal pressure lumen 2 located at the distal end 3 of catheter 1 and which is adapted for measuring the pressure of the arteria pulmonalis 4;

a proximal pressure lumen 5 located at about 30 cm of the distal end 3 and which is adapted for measuring the pressure of the right atrium 6;

a proximal pressure lumen 7 located at about 15 cm of the distal end of catheter 1 and which is adapted for measuring the pressure of the right ventricle 8;

a thermistor 9 located at about 4 cm of distal end of catheter 1;

a balloon 10 in order to measure the wedge pressure by means of lumen 2, when the balloon is inflated, through lumen L10;

pressure tubing lines K2, K5, K7 connected to lumen L2, L5 and L7 of catheter 1 and which are filled with sterilized fluids;

pressure transducers T2, T5, T7 measuring the pressure based on the Wheatstone bridge principles;

the pressure in the right atrium 6;

the pressure in the right ventricle 8;

the pressure in the pulmonary artery 4 and the wedge pressure at discrete time intervals, at the moment the balloon is inflated.

The calculation of the cardiac output coefficient $Q_{I,TR}$ of the individual I, is executed as follows:

During the diastolic period of the heartcycle, the bolus thermodilution cardiac output $CO_t$ value is measured simultaneously with the pressure difference $\Delta P_{TR}$ between right atrium 6 and right ventricle 8 by means of the same catheter 1.

The obtained cardiac output by thermodilution ($CO_t$) is the typical cardiac output for the individual at time t, and set to $CO_{,I,t}$.

The cardiac output of the right atrium is the amount of blood per time unit, which flows through the tricuspid valve. This amount can increase to 5 times the normal value in man.

Considering formula (6) we obtained:

$$CO_{I,t} = Q_{ITR,t} \sqrt{\Delta P_{TR,t}} \qquad [7]$$

$$\text{and in others words } Q_{ITR,t} = \frac{CO_{I,t}}{\sqrt{\Delta P_{TR,t}}}$$

This measurement will be repeated N times, by preference 5 times, out of which the mean value of the cardiac output coefficient $Q_{ITR}$ is derived as:

$$Q_{ITR} = \frac{\sum_{t=1}^{N} Q_{iTR,t}}{N} \qquad [8]$$

$Q_{ITR}$ being calculated it is sufficient to measure $\Delta P_{TR,}$ in a continuous matter, as the pressure difference between right atrium 6 and right ventricle 6, in order to calculate in a continuous matter the continuous cardiac output $Q_H$ considering (6), i.e.:

$$Q_H = Q_{ITR} \sqrt{\Delta P_{TR}} \qquad [9]$$

It should be noticed that, $\Delta P_{TR}$ has to be considered as the pressure difference during outflow through the right atrium by means of an haemodynamic monitor, which means during the period in which the right atrium pressure is greater than the right ventricle pressure. Two periods can be recognised, i.e. the active and the passive outflow period.

In the same way, it is possible to calculate continuously the cardiac output $Q_H$ at the pulmonary artery valve by means of the pressure difference $\Delta P_{PA}$ difference between right ventricle and pulmonary artery during the period of outflow through the pulmonary artery valve. The following formulas are valid:

$$[6] \text{ becomes } Q_{I,PA} = \frac{\sum_{t=1}^{N} Q_{I,PA,t}}{N} \quad [6']$$

with $Q_H$=the cardiac output;

$Q_{I,PA}$=the cardiac output coefficient of the individual at the pulmonary artery valve;

$\Delta P_{PA}$=the pressure difference over the pulmonary artery valve, which is the pressure difference between right ventricle and pulmonary artery during the outflow through the pulmonary artery valve. This outflow period is the systolic periods of the heartcycle.

$$[7] \text{ becomes } Q_{I,PA,t} = \frac{CO_{I,t}}{\sqrt{\Delta P_{PA,t}}} \quad [7']$$

$$[8] \text{ becomes } Q_{I,PA} = \frac{\sum_{t=1}^{N} Q_{I,PA,N}}{N} \quad [8']$$

$$[9] \text{ becomes } Q_H = Q_{I,PA}\sqrt{\Delta P_{PA}} \quad [9']$$

As the calculations over the tricuspid valve and the pulmonary artery related to the cardiac output, it will be possible to obtain also other parameters considering the equality of formula (9) and (9').

Such parameters can be the ejection fraction, the compliance, the afterload information or valve delays.

It has to be considered also from the blood velocity value, particulary when derived from the continuous measurement of the cardiac output value.

I claim:

1. A method for the measurement of cardiac output ($Q_H$) of a patient comprising the steps of:
   determining a cardiac output of the patent by thermodilution ($CO_{I,t}$);
   determining a first pressure difference ($\Delta P_{PA,t}$) over the pulmonary artery valve of the patient as the pressure difference between right ventricle of the patient and the pulmonary artery of the patient during the outflow of the pulmonary artery valve or systolic period;
   determining a cardiac output coefficient ($Q_{I,PA}$) from said cardiac output ($CO_{I,t}$) and said first pressure difference ($\Delta P_{PA,t}$); and
   determining the cardiac output ($Q_H$) of the patient from said cardiac output coefficient ($Q_{I,PA}$) and said first pressure difference ($\Delta P_{PA,t}$).

2. The method of claim 1, wherein said cardiac output ($Q_H$) of the patient is continuously determined using said cardiac output coefficient ($Q_{I,PA}$) and said first pressure difference ($\Delta P_{PA,t}$).

3. The method of claim 1, wherein said first pressure difference ($\Delta P_{PA,t}$) is determined by integrating the first pressure difference over a predetermined time period.

4. A method for the measurement of cardiac output ($Q_H$) of a patient, comprising the steps of:
   determining a cardiac output of the patient by thermodilution ($CO_{I,t}$);
   determining a second pressure difference ($\Delta P_{TR,t}$) over the tricuspid valve of the patient as the pressure difference between the right atrium of the patient and the right ventricle of the patient during the outflow of the tricuspid valve or diastolic period;
   determining a cardiac output coefficient ($Q_{I,TR}$) from said cardiac output ($CO_{I,t}$) and said second pressure difference ($\Delta P_{TR,t}$); and
   determining the cardiac output ($Q_H$) of the patient from said cardiac output coefficient ($Q_{I,TR}$) and said second pressure difference ($\Delta P_{TR,t}$).

5. The method of claim 4, wherein said cardiac output ($Q_H$) of the patient is continuously determined using said cardiac output coefficient ($Q_{I,TR}$) and said second pressure difference ($\Delta P_{TR,t}$).

6. The method of claim 4, wherein said second pressure difference ($\Delta P_{TR,t}$) is determined by integrating the second pressure difference over a predetermined time period.

7. An apparatus for the measurement of cardiac output of a patient, comprising:
   a catheter having a distal end and a plurality of lumen;
   a plurality of pressure tubing lines, each tubing line from said plurality of pressure tubing lines being connectable to a corresponding lumen from said plurality of lumen;
   a plurality of pressure transducers, each pressure transducer from said plurality of pressure transducers being connectable to a corresponding tubing line from said plurality of pressure tubing lines;
   monitoring means connectable to said pressure transducers, said monitoring means being provided for:
   determining a cardiac output of the patient by thermodilution ($CO_{I,t}$);
   determining a first pressure difference ($\Delta P_{PA,t}$) over the pulmonary artery valve of the patient as the pressure difference between the right ventricle of the patient and the pulmonary artery of the patient during the outflow of the pulmonary artery valve or systolic period;
   determining a cardiac output coefficient ($Q_{I,PA}$) from said cardiac output ($CO_{I,t}$) and said first pressure difference ($\Delta P_{PA,t}$); and
   determining the cardiac output ($Q_H$) of the patient from said cardiac output coefficient ($Q_{I,PA}$) and said first pressure difference ($\Delta P_{PA,t}$).

8. The apparatus of claim 7, wherein said plurality of pressure lumen comprises:
   a distal pressure lumen having an opening port located at the distal end of the catheter, said distal pressure lumen being adapted for measuring the pressure in the pulmonary artery of the patient;
   a first proximal pressure lumen on said catheter and being adapted for measuring the pressure of the right atrium of the patient;
   a second proximal pressure lumen on said catheter and being adapted for measuring the pressure of the right ventricle of the patient; and
   wherein said catheter further comprises:
   a thermistor having an opening port located in such a manner that the thermistor is located in the pulmonary artery of the patient when the distal pressure lumen is positioned to measure pressure in the pulmonary artery;
   a balloon; and
   a balloon inflation lumen connected to said balloon for inflating said balloon.

9. An apparatus for the measurement of cardiac output of a patient, comprising;
   a catheter having a distal end and a plurality of lumen;

a plurality of pressure tubing lines, each tubing line from said plurality of pressure tubing lines being connectable to a corresponding lumen from said plurality of lumen;

a plurality of pressure transducers, each pressure transducer from said plurality of pressure transducers being connectable to a corresponding tubing line from said plurality of pressure tubing lines;

monitoring means connectable to said pressure transducers, said monitoring means being provided for:
  determining a cardiac output of the patient by the thermodilution ($CO_{I,t}$);
  determining a second pressure difference ($Q_{I,TR}$) over the tricuspid valve of the patient as the pressure difference between the right atrium of the patient and the right ventricle of the patient during the outflow of the tricuspid valve or diastolic period;
  determining a cardiac output coefficient ($Q_{I,TR}$) from said cardiac output ($CO_{I,t}$) and said second pressure difference ($\Delta P_{TR,t}$); and
  determining the cardiac output ($Q_H$) of the patient from said cardiac output coefficient ($Q_{I,TR}$) and said second pressure difference ($\Delta P_{TR,t}$).

10. The apparatus of claim 9, wherein said plurality of pressure lumen comprises:

a distal pressure lumen having an opening port located at the distal end of the catheter, said distal pressure lumen being adapted for measuring the pressure in the pulmonary artery of the patient;

a first proximal pressure lumen of said catheter and being adapted for measuring the pressure of the right atrium of the patient;

a second proximal pressure lumen on said catheter and being adapted for measuring the pressure of the right ventricle of the patient; and wherein said catheter further comprises:
  a thermistor having an opening port located in such a manner that the thermistor is located in the pulmonary artery of the patient when the distal pressure lumen is positioned to measure pressure in the pulmonary artery;
  a balloon; and
  a balloon inflation lumen connected to said balloon for inflating said balloon.

11. A monitoring device for use with a catheter, said monitoring device comprising:

means for determining a cardiac output of the patient by thermodilution ($CO_{I,t}$);

means for determining a first pressure difference ($\Delta P_{PA,t}$) over the pulmonary artery valve of the patient as the pressure difference between right ventricle of the patient and the pulmonary artery of the patient during the outflow of the pulmonary artery valve or systolic period;

means for determining a cardiac output coefficient ($Q_{I,PA}$) from said cardiac output ($CO_{I,t}$) and said first pressure difference ($\Delta P_{PA,t}$); and means for determining the cardiac output ($Q_H$) of the patient from said cardiac output coefficient ($Q_{I,PA}$) and said first pressure difference ($\Delta P_{PA,t}$).

12. A monitoring device for use with a catheter, said monitoring device comprising;

means for determining a cardiac output of the patient by thermodilution ($CO_{I,t}$);

means for determining a second pressure difference ($\Delta P_{TR,t}$) over the tricuspid valve of the patient as the pressure difference between the right atrium of the patient and the right ventricle of the patient during the outflow of the tricuspid valve or diastolic period;

means for determining a cardiac output coefficient ($Q_{I,TR}$) from said cardiac output ($CO_{I,t}$) and said second pressure difference ($\Delta P_{TR,t}$); and means for determining the cardiac output ($Q_H$) of the patient from said cardiac output coefficient ($Q_{I,TR}$) and said second pressure difference ($\Delta P_{TR,t}$).

* * * * *